(12) United States Patent
Ritter et al.

(10) Patent No.: US 11,161,077 B2
(45) Date of Patent: Nov. 2, 2021

(54) FIBER MEMBRANE TUBE FOR MASS TRANSFER BETWEEN FLUIDS AND METHOD OF AND CORE WINDER FOR MAKING SAME

(71) Applicant: ENMODES GMBH, Aachen (DE)

(72) Inventors: Philine Ritter, Aachen (DE); Ralf Borchardt, Aachen (DE)

(73) Assignee: ENMODES GMBH, Aachen (DE)

( * ) Notice: Subject to any disclaimer, the term of this patent is extended or adjusted under 35 U.S.C. 154(b) by 0 days.

(21) Appl. No.: 16/604,578

(22) PCT Filed: May 17, 2018

(86) PCT No.: PCT/EP2018/000261
§ 371 (c)(1),
(2) Date: Oct. 11, 2019

(87) PCT Pub. No.: WO2019/007540
PCT Pub. Date: Jan. 10, 2019

(65) Prior Publication Data
US 2020/0122089 A1  Apr. 23, 2020

(30) Foreign Application Priority Data

Jul. 3, 2017  (DE) .......................... 102017006238.2

(51) Int. Cl.
*B01D 63/02* (2006.01)
*A61M 1/16* (2006.01)
*B01D 63/04* (2006.01)

(52) U.S. Cl.
CPC ......... *B01D 63/021* (2013.01); *A61M 1/1621* (2014.02); *A61M 1/1698* (2013.01);
(Continued)

(58) Field of Classification Search
CPC .................. B01D 63/021; B01D 63/04; B01D 2313/025; B01D 2313/08;
(Continued)

(56) References Cited

U.S. PATENT DOCUMENTS

| 3,690,465 A | * | 9/1972 | McGinnis | ............. | B01D 53/22 |
| | | | | | 210/321.88 |
| 4,220,489 A | * | 9/1980 | Coplan | .................. | B01D 53/22 |
| | | | | | 156/166 |

(Continued)

FOREIGN PATENT DOCUMENTS

| JP | S62172964 A | | 7/1987 |
| JP | WO2017051600 | * | 3/2017 |

*Primary Examiner* — Pranav N Patel
(74) *Attorney, Agent, or Firm* — Andrew Wilford

(57) ABSTRACT

The invention relates to a method for producing a device for a mass transfer between two fluids, wherein at least one hollow-fiber mat (9) is wound on an at least partly hollow core assembly (1, 1a, 1b, 2), and the formed coil is inserted into a housing (10). The assembly of the housing (10) and the coil is then sealed (10), in particular potted, with a sealant at the opposing axial ends in the regions between the hollow-fiber ends and the housing. The core assembly (1, 2) is made of at least two axially adjacent core parts (1, 1a, 1b, 2) arranged one behind the other, at least one (1, 1a, 1b) of which has a hollow design, and the core parts (1, 1a, 1b, 2) are kept in specified axial positions relative to each other, in particular at a distance to each other, by means of at least one aid element (7) at least over the period of the sealing process and preferably over the period of the winding process as well. After the sealing process and the removal of the at least one aid element (7), at least the axially end-face core parts (1, 1a, 2) are kept in their relative positions to each other by means of the sealant. The invention also relates to a coil, a core assembly, and a core system.

8 Claims, 2 Drawing Sheets

(52) U.S. Cl.
CPC ........ *B01D 63/04* (2013.01); *B01D 2313/025* (2013.01); *B01D 2313/08* (2013.01)

(58) Field of Classification Search
CPC ............ B01D 2313/105; B01D 29/073; B01D 2323/42; B01D 53/10–12; B01D 2201/4053; A61M 1/1621; A61M 1/1698
See application file for complete search history.

(56) References Cited

U.S. PATENT DOCUMENTS

| | | | |
|---|---|---|---|
| 5,263,982 A | | 11/1993 | Shimomura |
| 6,113,782 A | * | 9/2000 | Leonard ............... B01D 63/022 210/321.89 |
| 8,449,659 B2 | | 5/2013 | Taylor |
| 8,690,994 B2 | | 4/2014 | Taylor |
| 8,906,300 B2 | * | 12/2014 | Wang .................. A61M 1/1698 422/46 |
| 2018/0207344 A1 | | 7/2018 | Himatsu |

* cited by examiner

FIBER MEMBRANE TUBE FOR MASS TRANSFER BETWEEN FLUIDS AND METHOD OF AND CORE WINDER FOR MAKING SAME

CROSS REFERENCE TO RELATED APPLICATIONS

This application is the US-national stage of PCT application PCT/EP2018/000261 filed 17 May 2018 and claiming the priority of German patent application 102017006238.2 itself filed 3 Jul. 2017.

FIELD OF THE INVENTION

The invention relates to a method of making an apparatus for mass transfer between two fluids, for example between blood and an exchange medium, to such an apparatus, and to the wound body or core assembly used in manufacture of the apparatus.

BACKGROUND OF THE INVENTION

In making such a mass-transfer apparatus, at least one tubular-fiber mat is wound on an at least partially tubular core assembly and the resultant wound body is inserted into a casing, whereupon the assembly of casing and wound body is sealed, particularly potted, at its axially opposite ends with a sealant in the regions between the tubular-fiber ends and the casing.

The apparatus for mass transfer between two fluids, such as blood and an exchange medium, for example, typically comprises a casing and a wound body arranged therein of an at least partially tubular core assembly and at least one tubular-fiber mat that is wound onto same.

Apparatuses of the type mentioned and such a generic method for the preparation thereof are known in the art.

The tubular fibers of a tubular-fiber mat are material-permeable and thus allow the permeable walls to exchange a substance between the two fluids. So-called oxygenators for enriching blood with oxygen and depleting it of carbon dioxide represent common applications. Such apparatuses are used in dialysis as well.

In these applications, blood is thus one of the two fluids. In an oxygenator application, the other fluid can be an oxygen-carrying gas, for example, in which the $O_2$ partial pressure is greater than in the blood to be treated and the $CO_2$ partial pressure is less than in the blood to be treated.

In other applications, a provision can be made, for example, to degas ultrapure water for use in the manufacture of semiconductors, for instance. Likewise, an application can provide for liquid extraction of hexanol from an aqueous flow, for example with octanol as an extractant. In general, any and all applications are conceivable in which membrane contactors are used.

Such an apparatus can be used with two liquids or two gases, as well as with one liquid and one gas.

One known construction makes a provision that one or more tubular-fiber mats in which the material-permeable tubular fibers are fastened so as to be mutually spaced apart, by for example warp yarns, are wound onto a core assembly that is tubular in regions, in order to effect the inflow of one of the two fluids, blood, for example, into the casing of the apparatus through the tubular region.

The resultant wound body, that comprises the core assembly and the tubular-fiber mat around it, is inserted into a casing, usually with a tubular cylindrical shape, and then potted.

A specialist in this field understands "potting" as the sealing of the regions between the tubular fiber ends and the casing, particularly in such a way that, after sealing, a chamber is formed between the casing and the tubular-fiber outer surfaces through which one of the two fluids, particularly the fluid to be treated, for example blood, can flow, and the tubular core assembly that is tubular at least in some portions, forms an inlet or outlet passage of the chamber. Moreover, the fiber ends are to remain open axially on the front side, whereby the fibers allow exchange medium, preferably gaseous exchange medium, to flow through. The tubular-fiber interior thus forms the region in which the exchange medium flows, a chamber being formed between the outer surfaces of the tubular fibers and the inner surface of the casing in which the fluid to be treated, for example blood, can flow.

A fluid inlet (or, alternatively, fluid outlet) is formed by the tubular region in the core assembly that constitutes a particularly central passage that is axially open at the end. In the prior art, the passage arrangement is a one-piece element, and the passage that is open at one axial end ends before the oppositely situated axial end side of the core assembly and branches before this end in the radial direction into the chamber formed. A fluid outlet (or alternatively fluid inlet) can be in the casing wall.

Such one-piece core assemblies have the disadvantage that the fluid flow that is divided in the radial direction in the vicinity of the radial branching of the passage is not completely closed annularly, with the effect that regions form in this transitional portion that are traversed more and less well. Disadvantageous flows can occur in such variably flowed-through regions. In an application in which blood forms the fluid to be treated, thrombosis can be provoked in such regions.

OBJECT OF THE INVENTION

It is therefore an object of the invention to constructively optimize the fluidic transition between the preferably central passage in the core assembly and the chamber in the casing and to make a manufacturing method for optimized construction available.

SUMMARY OF THE INVENTION

This object is achieved with an apparatus for mass transfer between two fluids, such as blood and an exchange medium, for example, that, in accordance with the foregoing description, comprises a casing and a wound body arranged therein of an at least partially tubular core assembly and at least one tubular-fiber mat wound thereon, and in which, according to the invention, the core assembly comprises at least one tubular core part and at least one additional separate core part that is adjacent to a tubular core part, preferably to the only tubular core part, with at least and particularly only the axially end core parts being fixed in their axial position relative to one another by the sealing compound that seals off the regions between the tubular-fiber ends and the casing.

The "axially adjacent arrangements of the core parts" are understood to be juxtaposed in the direction of axial extension of the wound body. The adjacent core parts can touch one another, but in a preferred embodiment they are spaced apart from one another in the axial direction and thus do not come into contact.

According to the invention, the additional, preferably only additional, separate core part is not itself tubular and thus prevents the fluid (to be treated) from flowing in the axial direction out of the wound body because it forms an inflow surface across from the opening of a core part that is arranged axially in front of same in the direction of flow, particularly such an inflow surface that diverts the flow of fluid between axial and radial directions.

The essential aspect of the invention here is that, after flowing out of a tubular core part of the core assembly, the fluid, particularly blood, is able to move from the region between this tubular core part and the additional separate (nontubular) core part following it in the direction of flow over a substantially enlarged peripheral region, preferably over the entire circumference of the core assembly, i.e. in uninterrupted fashion over 360°, into the chamber of the apparatus.

The invention can provide only one tubular core part and a single additional separate, nontubular core part that are then both axially at the ends in the resultant wound body and thus fixed in position by the sealing compound.

Insofar as the invention provides more than one tubular core part in an axially adjacent arrangement, preferably at a spacing from one another, a provision can also be made, particularly in addition to the above-described embodiment, that the fluid is able to move in a region between two such core parts over a very large peripheral region, preferably over the entire circumference of the core assembly, i.e. in uninterrupted fashion over 360°, into the chamber of the apparatus.

In the case of a core assembly composed of at least three core parts, at least two of which are tubular and one of which forms the additional separate, nontubular core part, an embodiment is thus possible in which fluid transfer is achieved within the wound body at a minimum of two axially spaced-apart locations.

In an embodiment with at least three core parts, at least two of which are tubular and form mutually aligned passages with the tubular regions, at least one is not arranged at the end.

The invention can provide here that only the two end core parts are fixed in position by the sealing compound. The additional tubular core part arranged between these core parts remains unfixed by the sealing compound.

Fixation can be provided here, however, by frictional engagement between the core part and the tubular fibers, a material connection between the core part and the tubular fibers, through contact with the core parts arranged axially next to them on both sides, or also by magnetic retention force that acts on the core part that is not fixed with the sealing compound.

For example, a magnet may be in such a core part that generates repulsive forces in the respective axially end core parts with homopolar magnets. The bilaterally acting repulsive forces produced in this manner hold the core part in a position between the axially end core parts at a spacing from each of these end core parts.

However, the invention can also explicitly provide that the core part can be moved axially between the axially fixed end core parts, particularly between two end positions in which it abuts against one of the end core parts. Different flows can thus also be produced depending on the axially vertical operating position.

The above-described fluid deflection according to the invention produces a very uniform inflow with reduced risk, preferably completely eliminates risk of inefficient flow around the fibers. In particular, when the transition is continuous over 360°, this means that all of the tubular fibers in the inlet region are flowed against uniformly. In oxygenator applications, the risk of thrombosis can be reduced substantially.

The invention achieves a definition of the axial position of the core parts relative to one another, particularly of the spacing between the core parts and thus of the cross section of the transition region, in that the position of the initially loosely positioned core parts, at least of the axially end core parts, in the tubular-fiber wound body is established by the sealing compound that particularly bonds in a form-fitting and cohesive manner not only to the tubular-fiber outer surfaces, but also to the core parts.

In order to manufacture such an apparatus, the invention thus provides a method in which the core assembly is formed by at least two separate, preferably only two separate, axially adjacent core parts that are preferably spaced apart and arranged contactlessly in succession, at least one of which is tubular, and the core parts are held in a predetermined axial position relative to one another, particularly at a predetermined minimum axial spacing from one another, by at least one spacer element at least during the sealing period and preferably also during winding, and after sealing and removal of the spacer element, at least the axially end core parts, preferably all of the core parts are held by the sealant in their position relative to one another.

Here, the spacer element can also be provided not only in order to maintain the loose core parts in the predetermined position, in particular to limit the minimum axial spacing, but also to in order to align them with each other, in particular to exclude a possible axial tilt relative to one another.

However, the invention can also provide to achieve a specifically predetermined tilt between the core parts, particularly between a nontubular additional core part and the tubular core part lying in the direction of flow, for example one in which the two adjacent core parts also touch. A nonuniform inflow of the fluid into the chamber can thus be effected in a targeted manner. For example, this can be achieved by providing the spacer element with a contact surface against which the separate additional core part aligns itself with the tubular core part by bearing mechanically against it. Likewise, the spacer element can have two axial regions with mutually tilted, i.e. not coaxial, so that two tubular core parts can be positioned on regions that are oriented in different axial directions and thus aligned with one another, for example.

According to the invention, a wound body is thus formed during manufacture that comprises at least one tubular-fiber mat that is wound on a core assembly in which the core assembly has at least one tubular core part and one separate additional core part that is axially adjacent thereto and is preferably spaced axially therefrom in a contactless manner. The tubular-fiber mat is thus wound around the loose, axially not fixed core parts. In such a formed wound body that therefore represents an intermediate product during manufacture, the core parts can thus be moved initially relative to one another in the wound body, particularly in the direction of the wound body axis.

In a possible embodiment, the invention can provide that, during sealing that is performed particularly in a centrifuge, core parts that are accessible on the axial front ends of the wound body are fixed in place with respect to the axial position in the wound body by a respective spacer element that is axially outside the casing and wound body.

During sealing in a centrifuge, the axial direction of the apparatus or of the wound body is generally made to coincide with the radial direction of the centrifuge so as to urge the sealing compound to the radially outward axial end of the apparatus by the centrifugal forces. It must be ensured during this process that the core part that is located radially on the inside during centrifuging is prevented from slipping axially in the direction of larger radii.

The invention can provide here that the radially inner core part is attached to an associated spacer element, preferably by screwing. The core part located radially to the outside relative to the centrifuge can rest loosely against an associated spacer element or also be fastened in the centrifuge, for example by screwing.

Another embodiment that can also be used for sealing in centrifuges can provide that the core parts, preferably at least one tubular, particularly only one tubular core part, and an additional (nontubular) core part are maintained at a spacing during winding and/or sealing by a pin-shaped spacer element that is inserted into a respective tubular core part, preferably into the only tubular core part, and particularly fixed to the respective/only tubular core part so as to be stationary, preferably by screwing with the respective/only tubular core part, the additional core part being preferably brought into a predetermined axial position, preferably to a predetermined minimum spacing from the respective/only core part, through contact with the end of the spacer element facing toward the additional core part. Instead of the above-mentioned screwing, any other stationary attachment between the spacer element and a tubular core part can be used, for example any means of achieving a positive and/or nonpositive and/or frictional engagement.

The pin-shaped spacer element ensures here that the axial position is maintained during centrifuging, preferably that a predetermined minimum spacing between the core parts is not undershot. In particular, only the limitation of the minimum axial spacing is important here, because during centrifugation, the radially inner core part is subjected only to a force radially to the outside, and the force is absorbed by the contact on the spacer element.

Preferably, the invention can provide that the pin-shaped spacer element simultaneously forms a plug during sealing that seals the axially accessible opening of the respective/only tubular core part during sealing against exposure to the sealant. This enables the subsequent blood supply to be connected to the opening that has been maintained open.

In an embodiment in which more than one tubular core part is provided, the pin-shaped spacer element can have a plurality of axially spaced-apart regions, each of which is set up to receive a tubular core part, preferably in a stationary manner. For example, each region can have an external thread that corresponds to an internal thread of a respective core part.

A spacer element can also have an end region to which a first tubular core part can be fixed in place, for example by screwing or other nonpositive, frictional, or positive engagement. The spacer element can be designed to taper axially in diameter starting from this region toward the opposite end, so that a shoulder forms a contact surface for a subsequent additional tubular core part that is pushed onto the spacer element. The axial position thereof within the wound body to be created is thus defined by the shoulder.

In a development of all possible embodiments, according to the invention the pin-shaped spacer element preferably engages in some portions positively over the additional core part at its end contacting the additional core part. For example, the spacer element can have a recess for this purpose that engages over a projection of the additional core part that tapers toward the tubular core part, particularly in a positive manner.

Therefore, the additional core part is preferably embodied, regardless of the type of spacer element, with an inflow projection that tapers toward the tubular core part in order to deflect the flow radially. This projection can be conical, for example. Preferably, the projection tip rests in an opening region of the tubular core part that becomes larger in the direction of the additional core part, particularly like a funnel. Such an opening region that becomes larger like a funnel can also be provided in each of a plurality of tubular core parts.

The tip of the projection can fit into the recess of the exemplarily pin-shaped spacer element, thereby defining the axial position, particularly the axial spacing, while also enabling the projection to be centered in the tubular core part relative to the passage.

It is essential that the axial position of the core parts be maintained in a defined manner at least during sealing. Preferably, however, the invention can also provide for securing the core parts relative to one another during winding.

For example, during winding and/or sealing, the additional core part is held with a retention force on the pin-shaped holding element, particularly in such a way that prevents the spacing between the loose core parts not only from becoming smaller, but also from becoming larger.

For example, the retention force can be exerted by a pressure element located axially outside of the wound body that rests against the externally accessible end face of the additional core part that thus presses toward the tubular core part. During winding and/or sealing, the wound body can be enclosed between two pressure elements that respectively press on the axially accessible end faces of the core parts in opposite directions.

According to the invention the retention force is produced by an adhesive, particularly a nonhardening fluid that is between the surfaces of the pin-shaped spacer element and additional core part that engage positively over one another. The loose core parts are thus held axially in place by adhesion, whereas the spacer element can be removed after sealing by overcoming the adhesion.

It is also possible to use a magnetic attraction effect between the pin-shaped holding element and the additional core part or an axially underlying element. For example, a magnet can be provided in the spacer element, and an additional magnet can be placed axially behind the additional core part, so that an attractive force acts between the two that presses the additional core part toward the spacer element.

In another embodiment, the spacer element can be formed by a spacer that is axially between two core parts during winding and/or sealing, it being possible in particular for the spacer to be removed from the core assembly through the passage in the respective/only tubular core part.

For example, such a removable spacer can be formed by a rope wound body, the end of which is placed through the tubular core part. After winding of the tubular-fiber mat and the sealing, the end of the rope can be pulled, thereby unwinding the rope wound body between the core parts and enabling it to ultimately be removed in its entirety.

Likewise, in the embodiment of the spacer element as a spacer located between the core parts, but also in the above-described and all other possible embodiments, the possibility exists for a spacer element to be made of a material that is soluble in a solvent, preferably water, and is dissolved with the solvent after sealing, particularly washed out through the passage in the respective/only tubular core part. For example, a spacer element can be made of polyvinyl alcohol that is soluble in hot water.

In connection with the pin-shaped spacer element, the invention can form a core system that comprises a core assembly with at least one tubular core part and one core part that is separate therefrom that are particularly intended to remain in a tubular-fiber mat of an apparatus for mass transfer between two fluids, for example between blood and an exchange medium, after the winding of at least one tubular-fiber mat onto the core assembly and to define the direction of flow of one of the fluids, and that also comprises a spacer element that can be inserted into the tubular core part and fastened therein in an axially stationary manner, the spacer element having an axial length that is selected in order to define the axial position of the core parts relative to one another, particularly the minimum axial spacing between the core parts, through contact between the spacer element and the additional separate core part.

BRIEF DESCRIPTION OF THE DRAWING

The invention will be explained with reference to the following figures in preferred examples. Therein.

SPECIFIC DESCRIPTION OF THE INVENTION

Figure 1:
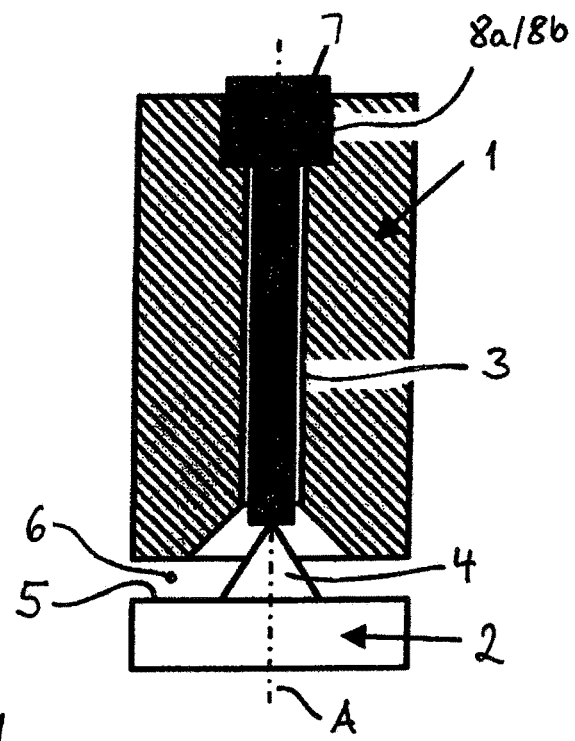
FIG. 1 is an axial section through a core assembly according to the invention.

FIG. 1 shows a core assembly according to the invention comprising a tubular, here upper core part 1 and an additional, nontubular, here lower core part 2. The two core parts 1 and 2 form separate individual elements that have no connection to each other, meaning that they do not touch directly and have a predetermined axial spacing between them.

The tubular core part 1 has a central passage 3 that leads to the upper and lower axial end faces. In the vicinity of the opening facing toward the additional core part 2, the opening becomes larger like a funnel toward the core part 2.

The core part 2 has a projection 4 that is tapered toward the tubular core part 1, here conically. The projection 4 is arranged, preferably centrally, on a planar end face 5 of the core part 2 directed toward the tubular core part 1. The tip of the projection engages axially into the flared region of the lower end of the core part 1 so that it is surrounded by the core part 1.

Figure 2:
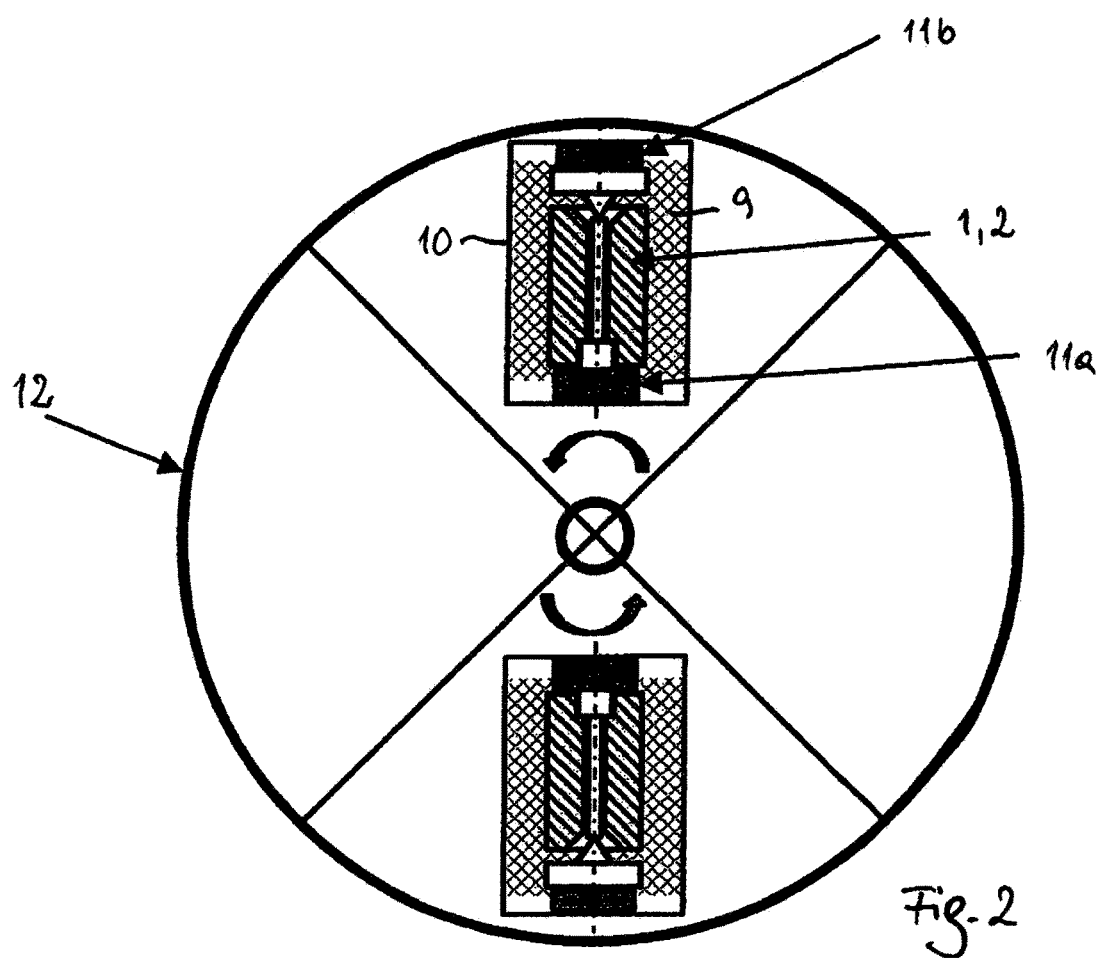
FIG. 2 illustrates the sealing process for manufacture of the core assembly.

Fluid flow through the passage 3 impinges against the projection of the core part 2 and is deflected by it through an annular gap 6 from axial flow into radial outward flow and thus enters over a full 360° a chamber that, in the finished apparatus, would be formed between the core assembly around which at least one tubular-fiber mat would be wound and the inner wall of a casing 10 (FIG. 2).

Instead of a conical shape, the projection 4 can also have any other tapered shape that is found to be aerodynamic, it being preferred, however, that this shape of the projection be rotationally symmetrical about a central axis A of the core assembly along which the passage 3 also particularly extends.

This possibility of flow over a full 360° constitutes an essential aspect of the apparatus according to the invention.

For assembly, according to the invention a pin-shaped spacer element 7 is used in the passage 3 of the core part 1. In this embodiment, the spacer element 7 has an external thread 8a at its upper end that corresponds to an internal thread 8b at the upper end of the passage 3. The spacer element 7 is axially fixed in the core part 1 by screwing.

The lower end of the spacer element 7 faces toward the core part 2 and forms a contact surface that engages the tip of the projection 4. This sets a predetermined minimum axial spacing between the core parts 1 and 2 even if forces act on them during sealing in a centrifuge.

At least one tubular-fiber mat 9 can be wound up on the core assembly that is formed in this manner in order to form a wound body according to the invention that can then be inserted into the casing 10 of the apparatus.

FIG. 2 illustrates the sealing process. Here, the core assembly 1, 2 is surrounded by at least one tubular-fiber mat 9 and inserted into the casing 10. The overall arrangement is clamped with the spacer element 7 between clamping elements 11a and 11b that act on the core parts 1, 2 with a force that is axial relative to the apparatus and radial relative to a centrifuge plate 12.

During centrifuging, sealing compound bonds to the radially outer core part, the local fiber ends, and the casing inner wall, thereby securing the relevant core part. The process is repeated for both axial ends of the apparatus. Both core parts are then axially fixed, and the spacer element 7 can be removed.

Figure 3:
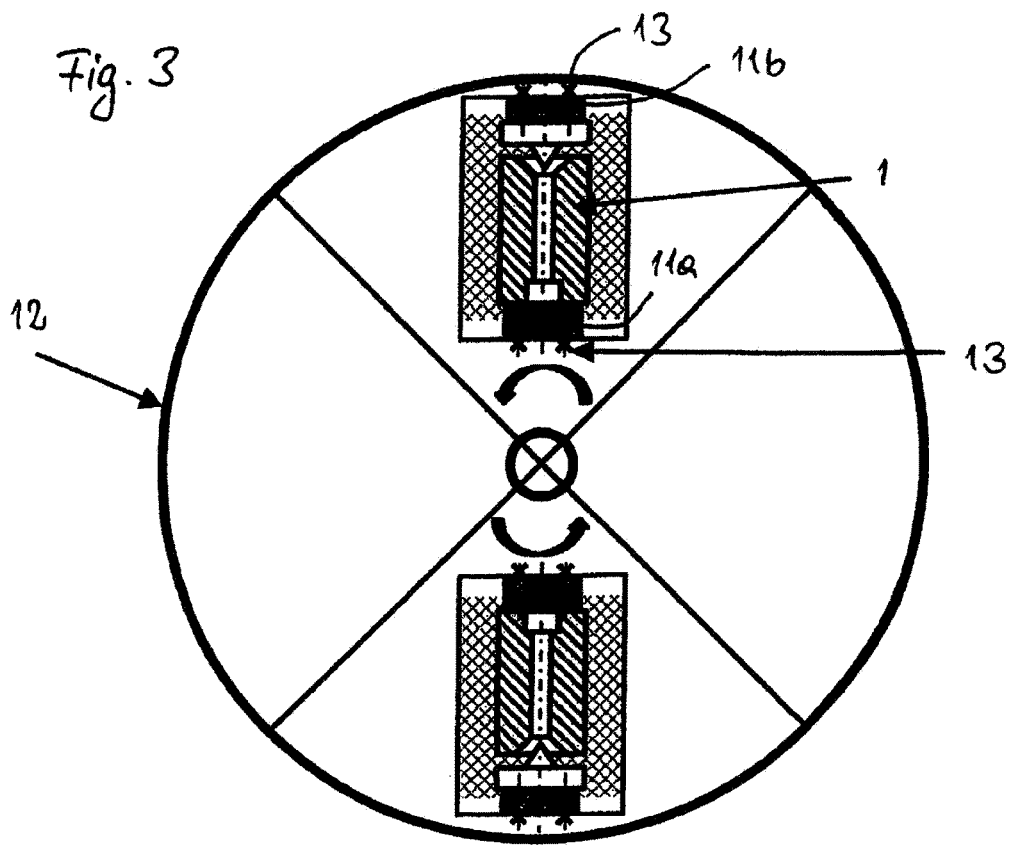
FIG. 3 shows an alternative sealing process.

FIG. 3 shows an alternative embodiment in which, instead of the use of a pin-shaped spacer element, at least the radially inner core part 1 is connected by screws 13 to the clamping element 11a, with the core part 2 preferably also being fastened by screws 13 to the clamping element 11b. The clamping elements 11a and 11b thus, according to the invention, fix the position of the core parts 1, 2, relative to one another during sealing until the sealing compound has solidified and provided for fixation.

Figure 4:
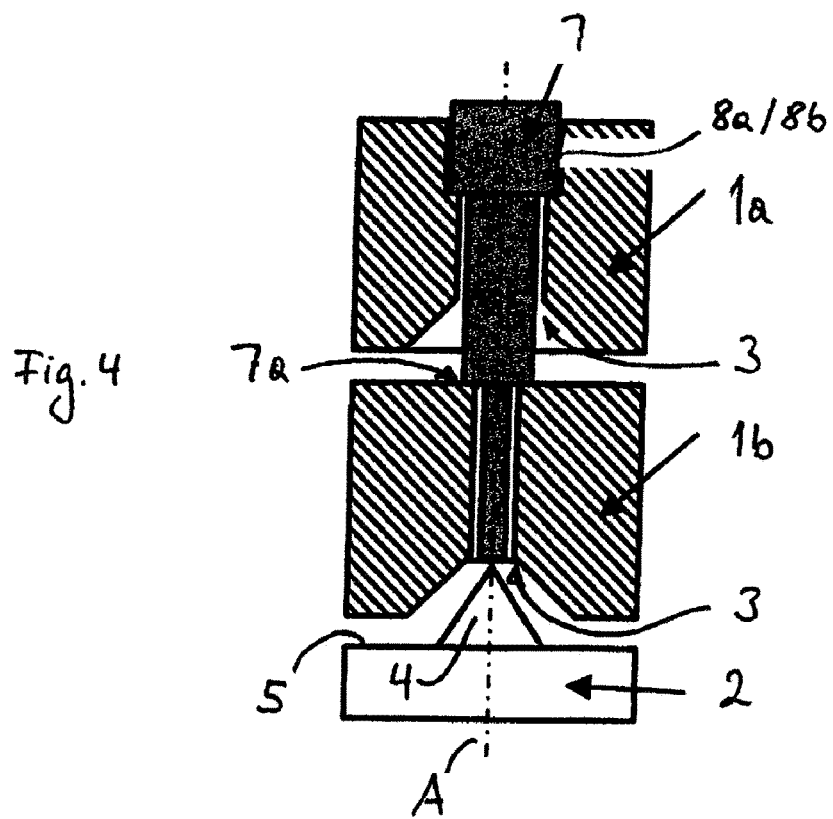
FIG. 4 is an axial section through another core assembly in accordance with the invention.

FIG. 4 shows an alternative core assembly to FIG. 1. Here, the core assembly comprises two axially spaced tubular core parts 1a and 1b and a separate additional and nontubular core part 2. All descriptions that are made to FIG. 1 apply to the upper core part 1a and the core part 2. Each tubular core part 1a or 1b has a central passage 3 that widens in a funnel shape toward the adjacent core part.

As in FIG. 1, the pin-shaped spacer element 7 also has an upper external thread region 8a here to which the first upper tubular core part 1a can be fastened with the corresponding internal thread 8b.

The pin-shaped spacer element 7 is formed with a shoulder to have a reduced diameter end region extending toward the additional nontubular core part 2. The shoulder 7a forms a stop against which the second tubular core part 1b can be pushed onto the pin-shaped spacer element 7. Its axial position is defined on this basis.

As in FIG. 1, the additional nontubular core part 2 comes to rest with its tip of the projection 4 against the lower axial end of the spacer element, so that its axial position is also defined in the wound body to be formed during subsequent sealing.

Sealing then takes place after the formation of the wound body as described in relation to FIG. 2 or 3.

The invention claimed is:

1. A method of making an apparatus for mass transfer between two fluids, the method comprising the steps of:
   a) providing two separate core parts of which one is tubular and extends along an axis;

b) holding the core parts axially apart and out of contact with each other;
c) winding a tubular-fiber mat on the axially spaced core parts to form a wound body extending along the axis;
d) inserting the wound body into a casing to form an assembly;
e) making the core parts accessible on axial outer ends of the wound body from axially outside the casing and the wound body;
f) orienting the assembly in a centrifuge such that during centrifuging one of the core parts is radially outside the other of the core parts and the radial inner core part is attached to an inner clamping element of the centrifuge while the radial outer core part engages an outer clamping element of the centrifuge;
g) rotating and centrifugally urging the radially outer core part against the outer clamping element by operation of the centrifuge while radially holding the inner core part in place with the inner clamping element;
h) potting the radially outer end of the rotating wound body with a sealant on the mat and the casing;
i) thereafter reversing the assembly by 180° between the clamping elements and repeating steps g) and h); and
j) thereafter removing the core parts from the clamping elements to leave the axially spaced core parts potted in the sealant spaced axially relative to one another.

2. The method according to claim 1, further comprising the step of, while maintaining the core parts in the predetermined axial position relative to one another during the winding step or the potting step,
inserting the spacer element into the tubular core part; and
fixing the spacer element in the tubular part so as to be stationary and bear axially on the other core part.

3. The method according to claim 2, wherein the spacer element is pin-shaped and simultaneously forms a plug that, during the potting step, axially closes a throughgoing opening of the tubular core part from exposure to the sealant.

4. The method according to claim 3, wherein the pin-shaped spacer element extends axially past the tubular core part and has at its end contacting the other core part a recess that engages over a projection of the other core part that tapers toward the tubular core part.

5. The method according to claim 2, further comprising the step of:
holding the other core part on the spacer element with a retention force during the winding step and the potting step.

6. The method according to claim 5, wherein the retention force is exerted by
a pressure element located axially outside the wound body that rests against a face of the externally accessible end of the other core part; or
an adhesive fluid that is between surfaces of the pin-shaped spacer element and the other core part that engage positively over one another; or
a magnetic attractive effect between the pin-shaped holding element and the other core part or an element lying axially behind it.

7. The method according to claim 1, wherein the spacer element is formed by a removable spacer axially between the core parts during the winding and the potting steps and removable from the core assembly through the tubular core part.

8. The method according to claim 2, wherein the spacer element is made of a material soluble in a solvent and the removing step is carried by
dissolving the spacer element with the solvent after the potting step and
washing the dissolved spacer element out through the tubular core part.

* * * * *